United States Patent
Yang et al.

(10) Patent No.: US 11,845,718 B2
(45) Date of Patent: Dec. 19, 2023

(54) PROCESS FOR PRODUCING P-XYLENE AND ETHYLBENZENE FROM $C_8$ AROMATIC CONTAINING ETHYLBENZENE

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Yanqiang Yang, Beijing (CN); Dehua Wang, Beijing (CN); Huiguo Wang, Beijing (CN); Jianfeng Ma, Beijing (CN); Hongchao Wang, Beijing (CN); Ben Li, Beijing (CN); Yusi Liu, Beijing (CN); Xiaofei Qiao, Beijing (CN); Ningning Gao, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

( * ) Notice: Subject to any disclaimer, the term of this patent is extended or adjusted under 35 U.S.C. 154(b) by 0 days.

(21) Appl. No.: 17/754,285

(22) PCT Filed: Sep. 28, 2020

(86) PCT No.: PCT/CN2020/118248
§ 371 (c)(1),
(2) Date: Mar. 29, 2022

(87) PCT Pub. No.: WO2021/057992
PCT Pub. Date: Apr. 1, 2021

(65) Prior Publication Data
US 2022/0332665 A1 Oct. 20, 2022

(30) Foreign Application Priority Data

Sep. 29, 2019 (CN) .......................... 201910932863.5

(51) Int. Cl.
C07C 7/13 (2006.01)
C07C 5/27 (2006.01)

(52) U.S. Cl.
CPC .............. *C07C 5/2737* (2013.01); *C07C 7/13* (2013.01); *C07C 2529/80* (2013.01)

(58) Field of Classification Search
CPC ..... C07C 15/073; C07C 15/08; C07C 5/2737; C07C 7/12; C07C 7/13; C07C 2529/44; C07C 2529/80
See application file for complete search history.

(56) References Cited

U.S. PATENT DOCUMENTS

| 6,369,287 B1 * | 4/2002 | Magne-Drisch ...... C07C 15/073 585/828 |
| 2002/0082461 A1 | 6/2002 | Magne-Drisch et al. |
| 2017/0166498 A1 * | 6/2017 | Weiss .................... C07C 5/2737 |

FOREIGN PATENT DOCUMENTS

| CN | 100506765 C | 7/2009 |
| CN | 101497022 B | 6/2011 |

(Continued)

OTHER PUBLICATIONS

Intellectual Property Office of Singapore; "Written Opinion for Application No. 11202203063S"; dated Oct. 9, 2023; pp. 1-5.

*Primary Examiner* — Sharon Pregler
(74) *Attorney, Agent, or Firm* — NKL Law; Allen Xue (57) ABSTRACT

A process for producing para-xylene and ethylbenzene from $C_8$ aromatics containing ethylbenzene includes the steps of sending $C_8$ aromatics containing ethylbenzene to an ethylbenzene liquid-phase adsorption separation device, wherein a suction liquid containing ethylbenzene and a suction (Continued)

residual liquid are obtained after the adsorption separation, and the desorbents in the suction liquid and the suction residual liquid are removed to obtain ethylbenzene and a suction residual oil; sending the suction residual oil to a para-xylene adsorption separation device, and unadsorbed components are discharged as a raffinate from the adsorbent bed; the adsorbent bed is rinsed with a desorbent to desorb the para-xylene therein and obtain an extract; the desorbents in the extract and the raffinate are respectively removed to obtain para-xylene and a raffinate oil; sending the raffinate oil to a xylene isomerization device to carry out xylene isomerization, and the isomerization product is fractionated.

21 Claims, 2 Drawing Sheets

(56) References Cited

FOREIGN PATENT DOCUMENTS

| | | | | | |
|---|---|---|---|---|---|
| CN | 104418698 | A | | 3/2015 | |
| CN | 103373891 | B | | 7/2015 | |
| CN | 103201240 | B | | 11/2015 | |
| CN | 103418422 | B | | 6/2016 | |
| CN | 104418687 | B | | 8/2016 | |
| CN | 106552582 | A | | 4/2017 | |
| CN | 106552852 | A | * | 4/2017 | ............ B21D 22/16 |
| CN | 105085136 | B | | 2/2020 | |
| CN | 112573985 | A | | 3/2021 | |
| CN | 113087585 | A | | 7/2021 | |
| CN | 1886357 | B | | 9/2021 | |
| JP | S6289636 | A | | 4/1987 | |

* cited by examiner

Prior Art

PROCESS FOR PRODUCING P-XYLENE AND ETHYLBENZENE FROM $C_8$ AROMATIC CONTAINING ETHYLBENZENE

FIELD OF THE INVENTION

The present invention relates to a process for producing para-xylene and ethylbenzene from $C_8$ aromatics containing ethylbenzene, concretely speaking, to a process for producing para-xylene and ethylbenzene through a liquid-phase adsorption separation combined process.

BACKGROUND OF THE INVENTION

Para-xylene is an important chemical material for producing terephthalic acid and dimethyl terephthalate used for synthesizing textile products and various plastic articles.

The sources of xylene mainly include coal tar fractions, petroleum reforming products and thermal cracking products, etc. A $C_8$ aromatic mixture rich in ethylbenzene and xylene can be obtained by rectification. The $C_8$ aromatics include ethylbenzene, para-xylene, meta-xylene, and ortho-xylene. In the prior art, para-xylene is mainly obtained by separation from the $C_8$ aromatics. To produce more para-xylene, the meta-xylene and ortho-xylene obtained by adsorption separation need to be converted into para-xylene and then recycled to the adsorption separation device to separate the para-xylene therein.

The improvement of the above para-xylene adsorption separation technology is an important direction of research in the art, which involves the improvement of not only each unit step, but also the whole system or the combination of multiple steps.

CN100506765C discloses a process for co-producing para-xylene and styrene: sending a feed containing xylene, ethylbenzene and $C_9$-$C_{10}$ hydrocarbons to a distillation column, separating $C_8$ aromatics and $C_9$-$C_{10}$ hydrocarbons therein by distillation, passing the said $C_8$ aromatics into an adsorption column of the simulated moving bed to separate para-xylene (PX) from the $C_8$ aromatics; other components enter an ethylbenzene dehydrogenation reaction zone to generate styrene from ethylbenzene, and styrene is separated from the dehydrogenation product; other unconverted ethylbenzene, meta-xylene and ortho-xylene contact with the catalyst for isomerization to carry out a liquid-phase isomerization reaction, and the product of the isomerization reaction is recycled to the distillation column.

CN1886357B discloses a process for producing para-xylene comprising one adsorption step and two isomerization steps: separating $C_8$ aromatics comprising ethylbenzene and xylene with a simulated moving bed comprising at least 5 zones into an extract comprising 90-95 wt % of para-xylene, an intermediate raffinate which is rich in ethylbenzene and a part of meta- and ortho-xylene, and a raffinate 2 which substantially contains meta- and ortho-xylene. The intermediate raffinate is subject to isomerization in the vapour phase to convert ethylbenzene into xylene and the raffinate 2 is subject to isomerization in the liquid phase at a low temperature.

CN103373891B discloses a process for producing para-xylene and ethylbenzene from $C_8$ aromatics by adsorption separation. The $C_8$ aromatics are separated by a liquid-phase adsorption to obtain an extraction oil containing para-xylene and a raffinate oil containing ethylbenzene, m-xylene and o-xylene, and the raffinate oil is separated by a gas-phase pressure swing adsorption to obtain ethylbenzene; the m-xylene and o-xylene obtained by the gas-phase pressure swing adsorption are subject to isomerization reactions under mild conditions.

CN103201240B discloses a process for the production of para-xylene: after the separation of para-xylene from $C_8$ aromatics, dividing a para-xylene-depleted material into two parts and processing them in a liquid phase isomerization unit and a vapor phase isomerization unit connected in parallel; and it is proved that in the examples that this operation manner can reduce the energy consumption in the production of para-xylene.

SUMMARY OF THE INVENTION

An object of the present invention is to provide a process for producing para-xylene and ethylbenzene from $C_8$ aromatics containing ethylbenzene, wherein raw material is firstly separated by adsorption to obtain ethylbenzene, then a para-xylene adsorption separation device is used to obtain para-xylene by separation, other xylene components are isomerized and then return to the para-xylene adsorption separation device. The process can result in a high-purity para-xylene and ethylbenzene.

The process for producing para-xylene and ethylbenzene from $C_8$ aromatics containing ethylbenzene provided in the present invention comprises the following steps:

(1) sending $C_8$ aromatics containing ethylbenzene to an ethylbenzene liquid-phase adsorption separation device, so that the ethylbenzene therein is adsorbed by an adsorbent in an ethylbenzene adsorbent bed, and unadsorbed components are discharged from the adsorbent bed as a suction residual liquid; rinsing the adsorbent bed with a desorbent to desorb the ethylbenzene therein and obtain a suction liquid, and removing the desorbents in the suction liquid and the suction residual liquid respectively to obtain ethylbenzene and a suction residual oil;

(2) sending the suction residual oil obtained in step (1) to a para-xylene adsorption separation device, wherein the para-xylene is adsorbed by an adsorbent in a para-xylene adsorbent bed, and unadsorbed components are discharged from the adsorbent bed as a raffinate; rinsing the adsorbent bed with a desorbent to desorb the para-xylene therein and obtain an extract, and removing the desorbents in the extract and the raffinate respectively to obtain a para-xylene product and a raffinate oil;

(3) sending the raffinate oil obtained in step (2) to a xylene isomerization device to carry out a xylene isomerization under an action of a xylene isomerization catalyst, fractionating the isomerization product, discharging $C_7$- aromatics obtained by the fractionation from the device, and using remaining aromatics as raw material for the adsorption separation device in step (2).

By arranging an ethylbenzene adsorption separation device to firstly separate ethylbenzene in the raw material to obtain a high-purity ethylbenzene product, then absorbing and separating the remaining $C_8$ aromatics with low ethylbenzene content to separate the para-xylene therein, and isomerizing the remaining $C_8$ aromatics, the process of the invention can effectively improve the adsorption separation efficiency of para-xylene, increase the yield of para-xylene, and produce a high-purity ethylbenzene as a by-product.

MODE OF CARRYING OUT THE INVENTION

The process of the present invention provides an ethylbenzene adsorption separation device in front of the device for the adsorption separation of $C_8$ aromatics so that the ethylbenzene in the $C_8$ aromatics raw material containing ethylbenzene and xylene is separated from xylene by adsorption, the obtained $C_8$ aromatics with low ethylbenzene content are then subject to a liquid-phase adsorption separation to separate para-xylene therein, then the remaining components are sent to an isomerization device for an isomerization reaction to generate para-xylene, and then the isomerization product is returned to the para-xylene adsorption separation device. The process reduces the content of ethylbenzene involved in the recycling in the circulation formed by the adsorption separation of para-xylene and the isomerization reaction, thereby making the para-xylene adsorption separation device more efficient, and the operation severity of the isomerization device reduced. Compared with the prior art, under the condition of the same output of para-xylene, the adsorbent, the isomerization catalyst and the $C_8$ aromatics raw material as used are all reduced, and the increased scale of the ethylbenzene adsorption separation device is small, which only needs a small amount of ethylbenzene adsorbent, and can result in a high-purity ethylbenzene product.

Both steps (1) and (2) of the process of the present invention preferably adopt the liquid-phase simulated moving bed device to adsorb and separate the target product, and the adsorbent is filled in the adsorption column of the liquid-phase simulated moving bed device via multiple beds. During the adsorption separation, the adsorbent beds in the adsorption column are divided into four functional zones by four charging and discharging materials: an adsorption feed, a desorbent, an extract, and a raffinate. The adsorbent beds between the desorbent and the extract are the desorption zone; the adsorbent beds between the extract and the adsorption feed are the purification zone; the adsorbent beds between the adsorption feed and the raffinate are the adsorption zone; and the adsorbent beds between the raffinate and the desorbent are the buffer zone.

Step (1) of the present invention preferably adopts the liquid-phase simulated moving bed device to adsorb and separate ethylbenzene in the $C_8$ aromatics containing ethylbenzene. The adsorption separation temperature is preferably 70 to 180° C., and the pressure is preferably 0.2 to 2.0 MPa.

The adsorption separation of ethylbenzene from the $C_8$ aromatics described in step (1) can be carried out by two schemes.

The ethylbenzene adsorbent used in the first scheme includes 95-99.5 mass % of CsNaX zeolite and 0.5-5 mass % of binder, wherein the molar ratio of Cs/Na is 1.5-10.0, preferably 2-6, and the desorbent is toluene. Refer to CN106552582B for the detailed preparation process of the ethylbenzene adsorbent.

In the first scheme, the number of adsorbent beds of the liquid-phase simulated moving bed device for the adsorption separation of ethylbenzene in step (1) is preferably 8 to 24. The ratio of the number of adsorbent beds in the four functional zones for the adsorption separation: the desorption zone, the purification zone, the adsorption zone and the buffer zone, is 16-26%: 37-47%: 20-30%: 7-17%. The water content in the desorbent is preferably not more than 15 ppm, more preferably 1 to 15 ppm, and the ratio of the volume flow of the desorbent used for the adsorption separation of ethylbenzene to the volume flow of the adsorption feed is preferably 0.6 to 5.0.

The ethylbenzene adsorbent used in the second scheme includes 95-99.5 mass % of X zeolite and 0.5-5 mass % of binder; the cation site of the X zeolite is occupied by Ba or Ba and K, and the desorbent is benzene.

Preferably, the $Na_2O$ content in the ethylbenzene adsorbent is less than 0.6 mass %. When the cation site of the X zeolite is occupied by Ba, the content of BaO in the adsorbent is preferably 35-45 mass %, and when the cation site of the X zeolite is occupied by Ba and K, the content of BaO in the adsorbent is preferably 25-35 mass % and the $K_2O$ content is preferably 7-10 mass %.

In the second scheme, the number of adsorbent beds of the liquid-phase simulated moving bed device for the adsorption separation of ethylbenzene in step (1) is preferably 8 to 24. The ratio of the number of adsorbent beds in the four functional zones for the adsorption separation: the desorption zone, the purification zone, the adsorption zone and the buffer zone, is 16-26%: 37-47%: 20-30%: 7-17%. The water content in the desorbent is preferably 50 to 100 ppm, more preferably 70 to 90 ppm, and the ratio of the volume flow of the desorbent used for the adsorption separation of ethylbenzene to the volume flow of the adsorption feed is preferably 0.6 to 3.0, more preferably 1.0 to 2.0.

Step (2) of the present invention preferably adopts the liquid-phase simulated moving bed to adsorb and separate para-xylene. The adsorption separation temperature is preferably 110 to 200° C., and the pressure is preferably 0.4 to 2.0 MPa.

The adsorbent for the adsorption separation in step (2) preferably includes 95-99.5 mass % of X zeolite and 0.5-5 mass % of binder, and the cation site of the X zeolite is occupied by Ba or Ba and K. Refer to CN101497022B for the detailed preparation process.

The binder in the adsorbent of the present invention is preferably kaolin.

Preferably, the desorbent used for the adsorption separation in step (2) is toluene or para-diethylbenzene.

The number of adsorbent beds in the adsorption column of the liquid-phase simulated moving bed used in step (2) is preferably 8 to 24. The ratio of the number of adsorbent beds in the four functional zones for the adsorption separation: the desorption zone, the purification zone, the adsorption zone and the buffer zone, is 16-26%: 37-47%: 20-30%: 7-17%.

The extraction oil and the raffinate oil are obtained after the desorbents in the extract and the raffinate in step (2) are removed. The extraction oil is a para-xylene product and the raffinate oil is rich in ortho-xylene and meta-xylene. Preferably, a rectification column is respectively used to separate the desorbents in the extract and the raffinate. The operating temperature and the pressure of the rectification column are determined according to the boiling point of the desorbent. It is also determined that the desorbent is discharged from the top or the bottom of the column, and the desorbent obtained by the rectification can be reused. Likewise, a rectification column can also be used in step (1) to respectively remove the desorbents in the suction liquid and the suction residual liquid to obtain the suction oil and the suction residual oil, wherein the suction oil is ethylbenzene.

Step (3) of the present invention isomerizes xylene of the raffinate oil obtained in step (2). The xylene isomerization reaction preferably has a temperature of 210-360° C. and preferably has a pressure of 0.1-4.0 MPa. The weight hourly space velocity of the raffinate oil passing through the catalyst is preferably 11-20 $h^{-1}$, and the hydrogen/hydrocarbon molar ratio is preferably 0-0.9. That is, the isomerization can be carried out under hydrogen or non-hydrogen conditions. When it is carried out under hydrogen conditions, the hydrogen/hydrocarbon molar ratio is preferably 0.1-0.9.

Since the ethylbenzene content in the feed of the isomerization device is greatly reduced, the operation severity of the isomerization can be reduced. During the gas-phase reaction, the temperature is preferably 330-360° C., the pressure is preferably 0.1-2.0 MPa, and the hydrogen/hydrocarbon molar ratio is preferably 0.2-0.9. During the liquid-phase reaction, the temperature is preferably 210-300° C., the pressure is preferably 1.5-4.0 MPa, and the reaction only needs to pass hydrogen below the solubility limit into the liquid-phase feed.

Due to the reduction of ethylbenzene content in xylene isomerization reactants and relatively mild reaction conditions, by-products such as benzene, toluene and $C_9+$ aromatics in the reaction products are relatively few, the fractionation load after the isomerization reaction is reduced, and the amounts of $C_7-$ aromatics (aromatics with the carbon atom number less than or equal to 7) and $C_9+$ aromatics as removed are both relatively small; in particular the amount of $C_9+$ aromatics is very small. Thus, it is unnecessary to set up a fractionation equipment to remove $C_9+$ aromatics, and only one fractionation column is used to separate $C_7-$ aromatics and $C_8+$ aromatics, wherein $C_7-$ aromatics are discharged from the device and $C_8+$ aromatics are used as the raw material of the adsorption separation device in step (2). The isomerization product can also be fractionated, preferably by two rectification columns. The obtained $C_7-$ aromatics and $C_9+$ aromatics are discharged from the device, and the $C_8$ aromatics are used as the raw material of the adsorption separation device in step (2).

The xylene isomerization catalyst in step (3) of the present invention preferably comprises 15-90 mass % of ZSM-5 and/or ZSM-11 zeolite and 10-85 mass % of alumina.

Preferably, the xylene isomerization catalyst comprises 15-90 mass % of ZSM-5 and/or ZSM-11 zeolite, 1-5 mass % of mordenite and 5-84 mass % of alumina. Its preparation process can be seen in CN103418422B.

Optionally, in step (2) of the process of the present invention, a stream of $C_8$ aromatics component with low ethylbenzene content is further externally added to the suction residual oil obtained in step (1).

The mass ratio of the externally added $C_8$ aromatics component with low ethylbenzene content to the suction residual oil obtained in step (1) is preferably 0.1 to 0.8.

The ethylbenzene content in the suction residual oil in step (1) and the $C_8$ aromatics component with low ethylbenzene content externally added in step (2) of the present invention is preferably not more than 3 mass %, more preferably not more than 2 mass %. The $C_8$ aromatics raw material with low ethylbenzene content can be one or more of a toluene disproportionation product, a toluene disproportionation and transalkylation product, and a toluene methanol methylation product.

In the present invention, the ethylbenzene content in the $C_8$ aromatics containing ethylbenzene in step (1) is preferably 10 to 30 mass %, more preferably 10 to 25 mass %. The $C_8$ aromatics raw material rich in ethylbenzene and xylene can be one or more of coal tar, reformate, transalkylation product and other materials containing $C_8$ aromatics compounds.

The invention is described in detail below in combination with the drawings.

Figure 1:
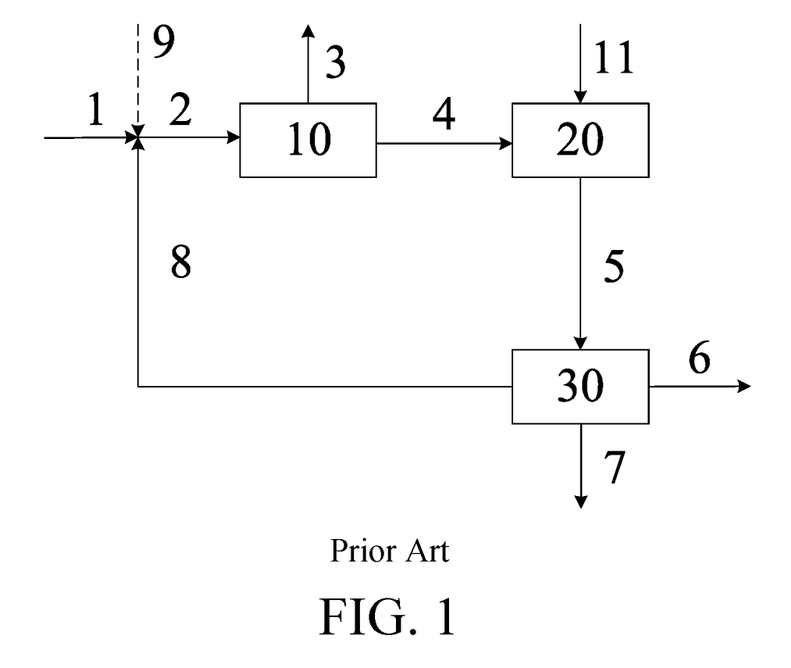
FIG. 1 is a flowchart of the production of para-xylene from $C_8$ aromatics in the prior art.

FIG. 1 is a flowchart of the production of para-xylene from $C_8$ aromatics in the prior art. $C_8$ aromatics containing ethylbenzene and xylene are mixed through pipeline 1 with the circulating materials from pipeline 8, and the mixture is sent to the para-xylene adsorption separation device 10 through pipeline 2. An extract rich in para-xylene is obtained after the adsorption separation. The desorbent in the extract is removed to obtain an extraction oil with para-xylene in a purity of 99.5 mass % or higher, which is discharged through pipeline 3 and is a para-xylene product. The obtained para-xylene-depleted $C_8$ aromatics material is the raffinate. The raffinate oil obtained after the desorbent is removed is sent through pipeline 4 to a gas-phase xylene isomerization device 20 for a xylene isomerization, and ortho-xylene and meta-xylene are converted into para-xylene. The desorbents in the extract and the raffinate obtained during the process are both removed by a rectification column (not shown in FIG. 1). Optionally, in the presence of hydrogen provided through pipeline 11, the gas-phase xylene isomerization process can convert ethylbenzene contained therein to form benzene and ethane or convert ethylbenzene into xylene close to the thermodynamic equilibrium. The product of the xylene isomerization is sent to a fractionation device 30 through pipeline 5, and generally two rectification columns are used for fractionation. The $C_7-$ aromatics material obtained by fractionation in the first fractionation column is discharged through pipeline 6, and the $C_9+$ aromatics material obtained in the second fractionation column is discharged through pipeline 7. The resulting $C_8$ aromatics are recycled to pipeline 2 through pipeline 8, and then enter the para-xylene adsorption separation device 10 through pipeline 2. Optionally, an externally added stream of $C_8$ aromatics with low ethylbenzene content is added to pipeline 2 from pipeline 9, and the ethylbenzene content in the externally added $C_8$ aromatics is lower than the ethylbenzene content in the $C_8$ aromatics entered from pipeline 1.

Figure 2:
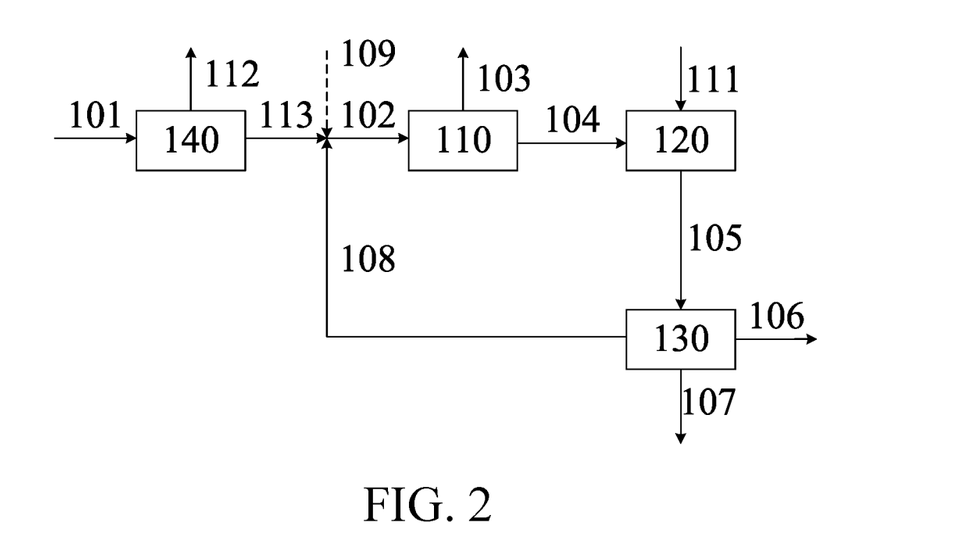
FIG. 2 is a flowchart of the production of para-xylene and ethylbenzene from $C_8$ aromatics in the present invention.

FIG. 2 is a flowchart of the production of ethylbenzene and para-xylene from $C_8$ aromatics in the present invention. $C_8$ aromatics containing ethylbenzene and xylene are sent to the adsorption column of an ethylbenzene liquid-phase adsorption separation device 140 through pipeline 101, wherein ethylbenzene is adsorbed by the ethylbenzene adsorbent in the adsorbent bed and unadsorbed components are discharged from the adsorbent bed as a raffinate. The adsorbent bed is rinsed with a desorbent to remove the ethylbenzene therein and obtain a suction liquid, and the desorbents in the suction liquid and the suction residual liquid as obtained are removed respectively by rectification via the rectification column as arranged. The resulting suction oil is discharged through pipeline 112, which is an ethylbenzene product, whose purity is greater than or equal to 99.85 mass %, and can also be greater than or equal to 99.9 mass %. The resulting suction residual oil is discharged from pipeline 113 and sent to a para-xylene adsorption separation device 110 through pipeline 102 (the adsorption column in the ethylbenzene liquid-phase adsorption separation device 140 and the rectification column for removing the desorbents in the suction liquid and the suction residual liquid are not shown).

The suction residual oil sent to the para-xylene adsorption separation device 110 leads to an extract rich in para-xylene after the adsorption separation. The desorbent in the extract is removed to obtain an extraction oil with para-xylene in a purity of 99.5 mass % or higher, which is discharged through pipeline 103 and is a para-xylene product. The obtained para-xylene-depleted $C_8$ aromatics material not absorbed by the adsorbent is a raffinate. The raffinate oil obtained after the desorbent therein is removed is sent through pipeline 104 to a xylene isomerization device 120 for xylene isomerization. The desorbents in the extract and the raffinate as obtained during the above adsorption separation process are respectively removed by rectification via the rectification column as arranged (not shown in FIG. 2). Since the ethylbenzene content in the material of the para-xylene adsorption separation device 110 is low, the efficiency of adsorption separation of para-xylene is improved, and the energy consumption is reduced.

The raffinate oil is sent through 104 to the xylene isomerization device 120 for xylene isomerization, and orthoxylene and meta-xylene are converted into para-xylene. The xylene isomerization can be carried out by a gas-phase or liquid-phase reaction. If the gas-phase isomerization reaction is adopted, optionally, an appropriate amount of hydrogen is supplied through pipeline 111 to prolong the service life of the catalyst. Due to the low content of ethylbenzene in the reactants sent to the xylene isomerization device 120 through pipeline 104, the isomerization reaction can be operated under mild conditions of a lower reaction temperature and hydrogen/hydrocarbon molar ratio, as can reduce xylene loss in the xylene isomerization reaction and reduce the operation cost.

The xylene isomerization product obtained from the xylene isomerization device 120 is sent through pipeline 105 to a fractionation device 130 for fractionation, preferably fractionation using a rectification column. The $C_7-$ aromatics material obtained by fractionation are discharged from pipeline 106; the $C_9+$ aromatics are discharged through pipeline 107; the $C_8$ aromatics are recycled to pipeline 102 through pipeline 108, and then enter the para-xylene adsorption separation device 110 through pipeline 102. Optionally, an externally added stream of $C_8$ aromatics with low ethylbenzene content is added to pipeline 102 from pipeline 109, and the ethylbenzene content in the externally added $C_8$ aromatics is lower than the ethylbenzene content in the $C_8$ aromatics entered from pipeline 101.

Since the xylene isomerization of the present invention produces few by-products, the fractionation device 130 may use two rectification columns to separate $C_7-$ aromatics and $C_9+$ aromatics respectively, or not remove $C_9+$ aromatics, but use one fractionation column to separate $C_7-$ aromatics and $C_8+$ aromatics. The $C_8+$ aromatics are recycled to pipeline 102 through pipeline 108, and then enter the para-xylene adsorption separation device 110 through pipeline 102.

The present invention is further illustrated by the following examples, but the present invention is not limited thereto.

Example 1

Para-xylene or ethylbenzene adsorbent B was prepared according to the process of Example 2 of CN101497022B.

(1) Production of X Zeolite with small crystal grains: 16.4 kg sodium meta-aluminate solution (therein the content of $Al_2O_3$ is 17.3 mass %, and the content of $Na_2O$ is 21.0 mass %), 11.0 kg deionized water and 2.9 kg sodium hydroxide were added into a 100 L synthesis tank. After the solid base was completely dissolved under stirring, 11.8 kg sodium silicate solution (therein the content of $SiO_2$ is 28.3 mass %, and the content of $Na_2O$ is 8.8 mass %) was added. The mixture was stirred until it was homogeneous, and stood for aging at 25° C. for 20 hours to give a directing agent.

255 kg sodium silicate solution, 1001 kg deionized water and 37 kg sodium hydroxide were added into a 2000 L tank at 25° C., and they were sufficiently mixed under stirring. 227 kg sodium meta-aluminate was added under stirring, then 15 kg directing agent was added. Keep stirring until a homogeneous mixture was achieved. The mixture was warmed to 100° C., and stood for crystallization for 4 hours. The product was washed with water until the pH value of the washing solution was less than 10. The product was filtered and then dried for 12 hours at 80° C. to give NaX zeolite. The molar ratio of $SiO_2/Al_2O_3$ of the zeolite was 2.19 as calculated from the unit cell constants, and the mean particulate size of the crystal grains was 0.7 micron as observed by the scanning electron microscope.

(2) Shaping by Rolling: 88 kg (on dry basis, the same hereinafter) NaX zeolite produced in step (1) was mixed homogeneously with 9 kg kaolin (produced by Linfen, Shanxi, China, the content of kaolinite is 90 mass %) and 3.4 kg sesbania powder to give a mixed powder. The mixed powder was placed in a turnplate. During rolling, a suitable amount of aqueous sodium carbonate solution with a concentration of 5.0 mass % was sprayed onto the powder, so that the solid mixed powder was agglomerated into pellets. The amount of the aqueous sodium carbonate solution sprayed during rolling was 28 mass % of the solid mixed powder. Pellets with diameters of 0.35-0.80 mm were obtained by sieving, and the pellets were dried at 80° C. for 10 hours and calcined at 540° C. for 4 hours under air stream.

(3) In-situ Crystallization: the above-mentioned calcined pellets were treated with a mixed solution of sodium hydroxide and sodium silicate in a volume ratio of liquid/solid of 2.0:1, wherein the said mixed solution comprises 4.3 mass % of $Na_2O$ and 2.1 mass % of $SiO_2$, and stood for 4.0 hours at 96° C. to allow the kaolin therein to crystallize into X zeolite in situ. The pellets obtained after the in-situ crystallization were washed with deionized water until the pH value of the washing solution was 9.0. After drying at 80° C. for 12 hours and calcining at 500° C. for 2 hours, its adsorptive capacity of toluene was 0.230 g/g, which was equivalent to that the content of X zeolite in the agglomerated pellets was 97.9 mass %, and the binder content was 2.1 mass %.

(4) Ion Exchange: After the in-situ crystallization and calcination, the pellets were ion-exchanged continuously in a conventional column with 0.18 moL/L barium nitrate solution as an exchange liquor. The barium ion-exchange was carried out for 10 hours under the normal pressure at 92° C., and 4.0 $h^{-1}$ of the volume space velocity of the exchange liquor. The volume ratio of the used barium nitrate solution to the pellets was 40:1. After the exchange was completed, the pellets were washed with the deionized water whose volume was 10 times the volume of the pellets, and were dried under nitrogen gas stream at 220° C. for 6 hours to give the adsorbent B. Its ignition loss was 4.5 mass %, as measured after calcination at 600° C. for 2 hours. $Na_2O$ was 0.55 mass % and BaO was 39.5 mass %.

Example 2

The xylene isomerization catalyst C was prepared according to the process of Example 9 of CN103418422B.

ZSM-11 zeolite with a molar ratio of $SiO_2/Al_2O_3$ of 70, mordenite (with a molar ratio of $SiO_2/Al_2O_3$ of 11) and γ-alumina powders were homogeneously mixed in a mass ratio of 58.5:1.5:40 on a dry basis, and the mixture was added with an aqueous nitric acid solution in a concentration of 2 mass % accounting for 50% of the total mass of the powders and molded by kneading, dried at 120° C. for 2 hours, calcined in air at 600° C. for 3 hours, and then ion-exchanged with an aqueous NH$_4$Cl solution in a concentration of 3 mass % at 90° C. for 3 hours. The solid was dried at 60° C. for 6 hours, and calcined at 500° C. in air for 4 hours to obtain a composite carrier a.

The composite carrier a was placed in a reactor and warmed up to 500° C., introduced with a water vapor-containing air for treatment for 8 hours. The volume space velocity of the air passing through the catalyst was 800 h$^{-1}$, and the water content in the air is 25 volume %, thereby obtaining a composite carrier b.

The composite carrier b was immersed with chloroplatinic acid solution in the liquid/solid volume ratio of 2:1 for 12 hours. The platinum content in the chloroplatinic acid solution should make the platinum content in the composite carrier be 0.02 mass % (relative to the carrier on a dry basis). The immersed solid was dried at 60° C. for 6 hours, and calcined at 500° C. in air for 4 hours to obtain a platinum-supported catalyst C, in which the platinum content based on the composite carrier was 0.02 mass %, and the composite carrier contained 58.5 mass % of HZSM-11 zeolite, 1.5 mass % of hydrogen-type mordenite, and 40 mass % of γ-alumina.

Example 3

Preparation of Ethylbenzene Adsorbent A

The agglomerated pellets with 97.9 mass % of X zeolite prepared in step (3) of Example 1 were placed in an exchange column, and exchanged with 0.5 mol/L of CsCl solution at 95° C., 0.1 MPa and a volume space velocity of exchange liquor of 4.0 h$^{-1}$ for 10 hours, the Cs ion exchange degree being 77 mol %. After the exchange was completed, the agglomerated pellets were washed with deionized water whose volume was 10 times the volume of the agglomerated pellets under the same conditions, and were then dried in air at 230° C. for 4 hours to give ethylbenzene adsorbent A. The molar ratio of Cs/Na was 3.4:1 and the ignition loss measured after the calcination at 600° C. for 2 hours was 0.5 mass %

Comparative Example 1

PX was produced from C$_8$ aromatics based on a scale of an annual output of 1000 kilotons of para-xylene according to the process in the prior art shown in FIG. 1.

C$_8$ aromatics rich in ethylbenzene and xylene from pipeline 1 and the xylene-isomerized C$_8$ aromatics from pipeline 8 were mixed and then entered the para-xylene adsorption separation device 10 through pipeline 2. After the adsorption separation of para-xylene, the obtained extraction oil was discharged from pipeline 3, which was a para-xylene product, and the obtained raffinate oil entered the xylene isomerization reaction device 20 through pipeline 4 for a gas-phase isomerization reaction. The hydrogen required for the reaction entered the xylene isomerization reaction device 20 through pipeline 11, and the reaction product entered the fractionation device 30 through pipeline 5. The fractionation device 30 was provided with two rectification columns. The C$_7$- aromatics material obtained by fractionation at the overhead of the first fractionation column was discharged from pipeline 6, and the components at the bottom entered the second fractionation column. The C$_9$+ aromatics obtained at the bottom were discharged from pipeline 7. The C$_8$ aromatics obtained overhead were returned by pipeline 8, and then entered the para-xylene adsorption separation device 10 by pipeline 2. The composition and the flow of the main pipeline materials are shown in Table 1.

The para-xylene adsorption separation device 10 is a liquid-phase simulated moving bed adsorption separation device. The adsorbent loaded in the adsorption column was the para-xylene adsorbent B in Example 1, with a loading amount of 1165 tons, an operating temperature of 170° C., and an operating pressure of 0.8 MPa. The desorbent was para-diethylbenzene. The number of adsorbent beds of the simulated moving bed was 24. The cycle period was 28 minutes. The numbers of adsorbent beds in the desorption zone, the purification zone, the adsorption zone and the buffer zone were respectively 5, 10, 6 and 3.

The catalyst loaded in the reactor of the xylene isomerization reaction device 20 was the isomerization catalyst C in Example 2, which was loaded in an amount of 57.3 tons. The temperature of the xylene isomerization reaction was 370° C. and the pressure was 0.6 MPa. The weight hourly space velocity of the feed to the reactor was 8 h$^{-1}$ and the hydrogen/hydrocarbon molar ratio was 1.0.

The bottom temperature of the first fractionation column was 161° C., the pressure was 0.04 MPa, and the plate number was 42.

The bottom temperature of the second fractionation column was 195° C., the pressure was 0.04 MPa, and the plate number was 51.

TABLE 1

| Material name | Flow, kiloton/year | Component content, mass % | | | |
|---|---|---|---|---|---|---|
| | | EB | PX | MX | OX | others |
| Pipeline 1 | 1262.4 | 17.00 | 19.00 | 40.00 | 24.00 | — |
| Pipeline 2 | 4661.3 | 6.14 | 21.85 | 48.94 | 21.87 | 1.20 |
| Pipeline 3 | 1000.0 | 0.04 | 99.80 | 0.10 | 0.06 | — |
| Pipeline 4 | 3661.3 | 7.80 | 0.56 | 62.28 | 27.82 | 1.54 |
| Pipeline 5 | 3666.2 | 1.95 | 21.23 | 48.45 | 19.54 | 8.83 |
| Pipeline 8 | 3398.9 | 2.10 | 22.90 | 52.26 | 21.08 | 1.66 | wherein EB—ethylbenzene, PX—para-xylene, MX—meta-xylene, OX—ortho-xylene.

Example 4

PX and ethylbenzene were produced from C$_8$ aromatics based on a scale of an annual output of 1000 kilotons of para-xylene according to the process of the present invention shown in FIG. 2.

C$_8$ aromatics rich in ethylbenzene and xylene were sent to the adsorption column of the ethylbenzene liquid-phase adsorption separation device 140 through pipeline 101, wherein ethylbenzene was adsorbed by the adsorbent in the ethylbenzene adsorbent bed and unadsorbed components were discharged from the adsorbent bed as a raffinate. The adsorbent bed was rinsed with a desorbent to remove the ethylbenzene therein and obtain a suction liquid, and the desorbents in the suction liquid and the suction residual liquid as obtained were removed respectively by rectification via the rectification column as arranged. The resulting suction oil was discharged through pipeline 112, which was an ethylbenzene product. The resulting suction residual oil was discharged from pipeline 113, mixed with C$_8$ aromatics in the isomerization product from pipeline 108 and sent to the para-xylene adsorption separation device 110 through pipeline 102. After the adsorption separation of para-xylene, the obtained extraction oil was discharged from pipeline 103, which was a para-xylene product, and the obtained raffinate oil entered the xylene isomerization reaction device 120 through pipeline 104 for a gas-phase isomerization reaction. The hydrogen required for the reaction entered the xylene isomerization reaction device 120 through pipeline 111, and the reaction product entered the fractionation device 130 through pipeline 105. The fractionation device 130 was provided with two rectification columns. The $C_7$- aromatics material obtained by fractionation at the overhead of the first fractionation column was discharged from pipeline 106, and the components at the bottom entered the second fractionation column. The $C_9$+ aromatics obtained at the bottom were discharged by pipeline 107. The $C_8$ aromatics obtained overhead were returned by pipeline 108, and then entered the para-xylene adsorption separation device 110 by pipeline 102. The composition and the flow of the main pipeline materials are shown in Table 2.

The adsorbent loaded in the adsorption column of the ethylbenzene liquid-phase adsorption separation device 140 was the ethylbenzene adsorbent A in Example 3, with a loading amount of 385 tons, an adsorption separation operation temperature of 110° C., and a pressure of 0.6 MPa. The desorbent was toluene, with water content of 5 ppm. The ratio of the volume flow of the desorbent in the adsorption column to the volume flow of the adsorption feed was 1.2. The number of adsorbent beds of the simulated moving bed was 16. The cycle period was 28 minutes. The numbers of adsorbent beds in the desorption zone, the purification zone, the adsorption zone and the buffer zone were respectively 3, 7, 4 and 2.

The para-xylene adsorption separation device 110 was a liquid-phase simulated moving bed adsorption separation device. The adsorbent loaded in the adsorption column was the para-xylene adsorbent B in Example 1, with a loading amount of 990 tons, an operating temperature of 170° C., and an operating pressure of 0.8 MPa. The desorbent was para-diethylbenzene. The number of adsorbent beds of the simulated moving bed was 24. The cycle period was 28 minutes. The numbers of adsorbent beds in the desorption zone, the purification zone, the adsorption zone and the buffer zone were respectively 5, 10, 6 and 3.

The catalyst loaded in the reactor of the xylene isomerization reaction device 120 was the isomerization catalyst C in Example 2, which was loaded in an amount of 35.3 tons. The temperature of the xylene isomerization reaction was 350° C. and the pressure was 0.5 MPa. The weight hourly space velocity of the feed to the reactor was 12 h$^{-1}$ and the hydrogen/hydrocarbon molar ratio was 0.8.

The first fractionation column, the second fractionation column and the operating conditions are all the same as those in Comparative Example 1.

TABLE 2

| Material name | Flow, kiloton/year | Component content, mass % | | | | |
|---|---|---|---|---|---|---|
| | | EB | PX | MX | OX | others |
| Pipeline 101 | 1234.9 | 17.00 | 19.00 | 40.00 | 24.00 | — |
| Pipeline 112 | 199.7 | 99.85 | 0.06 | 0.05 | 0.04 | — |
| Pipeline 113 | 1035.2 | 1.01 | 22.65 | 47.72 | 28.62 | — |
| Pipeline 102 | 4401.8 | 0.37 | 23.14 | 52.01 | 23.26 | 1.22 |
| Pipeline 103 | 1000.0 | 0.01 | 99.80 | 0.12 | 0.07 | — |
| Pipeline 104 | 3401.8 | 0.47 | 0.60 | 67.27 | 30.08 | 1.58 |
| Pipeline 105 | 3406.0 | 0.17 | 23.01 | 52.73 | 21.36 | 2.73 |
| Pipeline 108 | 3366.6 | 0.17 | 23.28 | 53.35 | 21.61 | 1.59 |

Comparisons of the consumption of raw materials and the loadings of the adsorbent and the catalyst in Comparative Example 1 and Example 4 are shown in Table 3. As can be seen from Table 3, for a para-xylene device with an annual output of 1000 kilotons, according to the process of Example 4 compared with the process of Comparative Example 1, the raw material consumption was reduced by 2.2%; the total loading of the isomerization catalyst C was reduced by 22 tons in total, which was a reduction of 38.4%; the loading of the para-xylene adsorbent B was reduced by 175 tons in total, which was a reduction of 15%; the loading of the ethylbenzene adsorbent increased by 385 tons, giving an output of ethylbenzene of 199.7 kilotons per year. Ethylbenzene had a purity of 99.85 mass % and a yield of 95 mass %.

TABLE 3

| | Comparative Example 1 | Example 4 |
|---|---|---|
| High-ethylbenzene $C_8$ aromatics raw material, kilotons/year | 1262.4 | 1234.9 |
| Total loading of isomerization catalyst C, tons | 57.3 | 35.3 |
| Total loading of para-xylene adsorbent B, tons | 1165 | 990 |
| Total loading of ethylbenzene adsorbent A, tons | — | 385 |
| Output of para-xylene, kilotons/year | 1000 | 1000 |
| Output of ethylbenzene, kilotons/year | — | 199.7 |

Example 5

PX and ethylbenzene were produced from $C_8$ aromatics based on a scale of an annual output of 1000 kilotons of para-xylene according to the process of Example 4, except that the adsorbent loaded in the adsorption column of the ethylbenzene liquid-phase adsorption separation device 140 was the ethylbenzene adsorbent B in Example 1, with a loading of 338 tons, an adsorption separation operation temperature of 135° C., and a pressure of 0.6 MPa, the desorbent was benzene with water content of 80 ppm, and the ratio of the volume flow of the desorbent in the adsorption column to the volume flow of the adsorption feed was 1.5. The number of adsorbent beds of the simulated moving bed was 24. The cycle period was 28 minutes. The numbers of adsorbent beds in the desorption zone, the purification zone, the adsorption zone and the buffer zone were respectively 5, 10, 6 and 3. Ethylbenzene had a purity of 99.86 mass % and a yield of 97 mass %.

The composition and the flow of the main pipeline materials are shown in Table 4. Comparisons of the consumption of raw materials and the loadings of the adsorbent and the catalyst are shown in Table 10.

TABLE 4

| Material name | Flow, kiloton/year | Component content, mass % | | | | |
|---|---|---|---|---|---|---|
| | | EB | PX | MX | OX | Others |
| Pipeline 101 | 1234.9 | 17.00 | 19.00 | 40.00 | 24.00 | — |
| Pipeline 112 | 203.9 | 99.86 | 0.04 | 0.08 | 0.02 | — |
| Pipeline 113 | 1031.0 | 0.61 | 22.75 | 47.90 | 28.74 | — |
| Pipeline 102 | 4395.2 | 0.22 | 23.17 | 52.09 | 23.30 | 1.22 |
| Pipeline 103 | 1000.0 | 0.01 | 99.80 | 0.12 | 0.07 | — |
| Pipeline 104 | 3395.2 | 0.28 | 0.60 | 67.40 | 30.14 | 1.58 |
| Pipeline 105 | 3399.3 | 0.10 | 23.06 | 52.83 | 21.40 | 2.61 |
| Pipeline 108 | 3364.2 | 0.10 | 23.30 | 53.38 | 21.63 | 1.59 |

Comparative Example 2

PX was produced from $C_8$ aromatics following the process shown in FIG. 1 according to the process of Comparative Example 1, except that a stream of $C_8$ aromatics with low ethylbenzene content was externally added by pipeline 9 and mixed with $C_8$ aromatics entered by pipeline 1 and entered the para-xylene adsorption separation device 10 through pipeline 2. The composition and the flow of the main pipeline materials are shown in Table 5.

The operations of the para-xylene adsorption separation device 10 are the same as those in Comparative Example 1, except that the loading of the para-xylene adsorbent B was 1138 tons.

The operations of the xylene isomerization reaction device 20 are the same as those in Comparative Example 1, except that the loading of the catalyst C was 55.5 tons.

TABLE 5

| Material name | Flow, kiloton/year | Component content, mass % | | | | |
|---|---|---|---|---|---|---|
| | | EB | PX | MX | OX | Others |
| Pipeline 1 | 792.2 | 17.00 | 19.00 | 40.00 | 24.00 | — |
| Pipeline 9 | 396.1 | 1.50 | 23.20 | 53.10 | 22.20 | — |
| Pipeline 2 | 4550.5 | 4.12 | 22.38 | 50.49 | 21.80 | 1.21 |
| Pipeline 3 | 1000.0 | 0.03 | 99.80 | 0.11 | 0.06 | — |
| Pipeline 4 | 3550.5 | 5.27 | 0.57 | 64.69 | 27.92 | 1.55 |
| Pipeline 5 | 3555.1 | 1.32 | 21.83 | 49.80 | 20.08 | 6.97 |
| Pipeline 8 | 3362.2 | 1.39 | 23.08 | 52.65 | 21.24 | 1.64 |

Example 6

PX and ethylbenzene were produced from $C_8$ aromatics following the process shown in FIG. 2 according to the process of Example 4, except that a stream of $C_8$ aromatics with low ethylbenzene content was externally added by pipeline 109 and mixed with the suction residual oil entered by pipeline 113 and then entered the para-xylene adsorption separation device 110 through pipeline 102. The composition and the flow of the main pipeline materials are shown in Table 6.

The operations of the ethylbenzene liquid-phase adsorption separation device 140 are the same as those in Example 4, except that the loading of the adsorbent A was 242 tons.

The operations of the para-xylene adsorption separation device 110 are the same as those in Example 4.

The operations of the xylene isomerization reaction device 120 are the same as those in Example 4, except that the loading of the catalyst C was 35.1 tons.

TABLE 6

| Material name | Flow, kiloton/year | Component content, mass % | | | | |
|---|---|---|---|---|---|---|
| | | EB | PX | MX | OX | Others |
| Pipeline 101 | 774.9 | 17.00 | 19.00 | 40.00 | 24.00 | — |
| Pipeline 109 | 387.4 | 1.50 | 23.20 | 53.10 | 22.20 | — |
| Pipeline 112 | 125.3 | 99.85 | 0.06 | 0.05 | 0.04 | — |
| Pipeline 113 | 649.5 | 1.01 | 22.65 | 47.72 | 28.62 | — |
| Pipeline 102 | 4393.9 | 0.43 | 23.18 | 52.47 | 22.70 | 1.22 |
| Pipeline 103 | 1000.0 | 0.01 | 99.80 | 0.12 | 0.07 | — |
| Pipeline 104 | 3393.9 | 0.56 | 0.60 | 67.91 | 29.36 | 1.57 |
| Pipeline 105 | 3398.0 | 0.20 | 22.99 | 52.69 | 21.34 | 2.78 |
| Pipeline 108 | 3356.9 | 0.20 | 23.28 | 53.32 | 21.61 | 1.59 |

Comparisons of the consumption of raw materials and the loadings of the adsorbent and the catalyst in Comparative Example 2 and Example 6 are shown in Table 7. As can be seen from Table 7, for a para-xylene device with an annual output of 1000 kilotons, according to the process of Example 6 compared with the process of Comparative Example 2, the raw material consumption was reduced by 2.2%; the total loading of the isomerization catalyst C was reduced by 20.4 tons in total, which was a reduction of 36.7%; the loading of the para-xylene adsorbent B was reduced by 148 tons in total, which was a reduction of 13.0%; the loading of the ethylbenzene adsorbent increased by 242 tons, giving an output of ethylbenzene of 125.3 kilotons per year.

TABLE 7

| | Comparative Example 2 | Example 6 |
|---|---|---|
| $C_8$ aromatics raw material with high ethylbenzene content, kilotons/year | 792.2 | 774.9 |
| $C_8$ aromatics raw material with low ethylbenzene content, kilotons/year | 396.1 | 387.4 |
| Total loading of isomerization catalyst C, tons | 55.5 | 35.1 |
| Total loading of para-xylene adsorbent B, tons | 1138 | 990 |
| Total loading of ethylbenzene adsorbent A, tons | — | 242 |
| Output of para-xylene, kilotons/year | 1000 | 1000 |
| Output of ethylbenzene, kilotons/year | — | 125.3 |

Example 7

PX and ethylbenzene were produced according to the process of Example 5, except that the desorbent had water content of 40 ppm, ethylbenzene obtained by separation had a purity of 99.85 mass % and the yield of ethylbenzene was 93.2 mass %. The composition and the flow of the main pipeline materials are shown in Table 8. Comparisons of the consumption of raw materials and the loadings of the adsorbent and the catalyst are shown in Table 10.

TABLE 8

| Material name | Flow, kiloton/year | Component content, mass % | | | | |
|---|---|---|---|---|---|---|
| | | EB | PX | MX | OX | Others |
| Pipeline 101 | 1234.9 | 17.00 | 19.00 | 40.00 | 24.00 | — |
| Pipeline 112 | 196.0 | 99.85 | 0.04 | 0.08 | 0.03 | — |
| Pipeline 113 | 1038.9 | 1.37 | 22.58 | 47.53 | 28.52 | — |
| Pipeline 102 | 4407.6 | 0.50 | 23.11 | 51.95 | 23.23 | 1.21 |
| Pipeline 103 | 1000.0 | 0.01 | 99.80 | 0.12 | 0.07 | — |
| Pipeline 104 | 3407.6 | 0.64 | 0.60 | 67.16 | 30.03 | 1.57 |
| Pipeline 105 | 3411.7 | 0.23 | 22.97 | 52.64 | 21.33 | 2.83 |
| Pipeline 108 | 3368.6 | 0.23 | 23.27 | 53.31 | 21.60 | 1.59 |

Example 8

PX and ethylbenzene were produced from $C_8$ aromatics according to the process of Example 5, except that the desorbent had water content of 120 ppm, ethylbenzene obtained by separation had a purity of 99.85 mass % and the yield of ethylbenzene was 89 mass %. The composition and the flow of the main pipeline materials are shown in Table 9. Comparisons of the consumption of raw materials and the loadings of the adsorbent and the catalyst are shown in Table 10.

TABLE 9

| Material name | Flow, kiloton/year | Component content, mass % | | | | |
|---|---|---|---|---|---|---|
| | | EB | PX | MX | OX | Others |
| Pipeline 101 | 1234.9 | 17.00 | 19.00 | 40.00 | 24.00 | — |
| Pipeline 112 | 192.8 | 99.85 | 0.05 | 0.08 | 0.02 | — |
| Pipeline 113 | 1042.1 | 1.67 | 22.51 | 47.38 | 28.44 | — |
| Pipeline 102 | 4412.5 | 0.61 | 23.08 | 51.89 | 23.21 | 1.21 |
| Pipeline 103 | 1000.0 | 0.01 | 99.80 | 0.12 | 0.07 | — |

TABLE 9-continued

| Material name | Flow, kiloton/year | Component content, mass % | | | | |
|---|---|---|---|---|---|---|
| | | EB | PX | MX | OX | Others |
| Pipeline 104 | 3412.5 | 0.78 | 0.60 | 67.06 | 29.99 | 1.57 |
| Pipeline 105 | 3416.6 | 0.27 | 22.94 | 52.56 | 21.30 | 2.93 |
| Pipeline 108 | 3370.4 | 0.28 | 23.26 | 53.28 | 21.59 | 1.59 |

TABLE 10

| | Example 5 | Example 7 | Example 8 |
|---|---|---|---|
| High-ethylbenzene $C_8$ aromatics raw material, kilotons/year | 1234.9 | 1236.2 | 1236.5 |
| Total loading of isomerization catalyst C, tons | 35.3 | 35.3 | 35.3 |
| Total loading of para-xylene adsorbent B, tons | 990 | 990 | 990 |
| Total loading of ethylbenzene adsorbent B, tons | 338 | 338 | 338 |
| Output of para-xylene, kilotons/year | 1000 | 1000 | 1000 |
| Output of ethylbenzene, kilotons/year | 203.9 | 196.0 | 192.8 |
| Purity of ethylbenzene product, mass % | 99.86 | 99.85 | 99.85 |

Example 9

Preparation of Ethylbenzene Adsorbent D.

The ethylbenzene adsorbent B obtained in Example 1 was ion-exchanged in a tank reactor. The exchange solution was a potassium chloride solution of 0.4 mol/L. Ion-exchanges were carried out three times at 95° C. and 0.1 MPa. The liquid/solid volume ratio of the exchange solution and the ethylbenzene adsorbent B used every time was 4.5, and the ethylbenzene adsorbent D was produced after drying in a nitrogen stream at 205° C. for 4 hours. Its ignition loss was 4.8 mass %, as measured after calcination at 600° C. for 2 hours. $Na_2O$ was 0.43 mass %, BaO was 28.2 mass %, and $K_2O$ was 8.7 mass %.

Example 10

PX and ethylbenzene were produced from $C_8$ aromatics based on a scale of an annual output of 1000 kilotons of para-xylene according to the process of Example 4, except that the adsorbent loaded in the adsorption column of the ethylbenzene liquid-phase adsorption separation device 140 was the ethylbenzene adsorbent D in Example 9, with a loading of 298 tons, an adsorption separation operation temperature of 135° C., and a pressure of 0.8 MPa, the desorbent was benzene with water content of 80 ppm, and the ratio of the volume flow of the desorbent to the volume flow of the adsorption feed in the adsorption column was 1.3. The number of adsorbent beds of the simulated moving bed was 16. The cycle period was 26 minutes. The numbers of adsorbent beds in the desorption zone, the purification zone, the adsorption zone and the buffer zone were respectively 3, 7, 4 and 2. The composition and the flow of the main pipeline materials are shown in Table 11. Ethylbenzene had a purity of 99.86 mass % and a yield of 97.4 mass %.

TABLE 11

| Material name | Flow, kiloton/year | Component content, mass % | | | | |
|---|---|---|---|---|---|---|
| | | EB | PX | MX | OX | Others |
| Pipeline 101 | 1234.9 | 17.00 | 19.00 | 40.00 | 24.00 | — |
| Pipeline 112 | 204.8 | 99.86 | 0.05 | 0.05 | 0.04 | — |
| Pipeline 113 | 1030.1 | 0.53 | 22.77 | 47.94 | 28.76 | — |
| Pipeline 102 | 4394.0 | 0.19 | 23.18 | 52.11 | 23.30 | 1.22 |
| Pipeline 103 | 1000.0 | 0.01 | 99.80 | 0.12 | 0.07 | — |
| Pipeline 104 | 3394.0 | 0.24 | 0.60 | 67.43 | 30.15 | 1.58 |
| Pipeline 105 | 3398.1 | 0.09 | 23.07 | 52.85 | 21.41 | 2.58 |
| Pipeline 108 | 3363.8 | 0.09 | 23.30 | 53.39 | 21.63 | 1.59 |

The invention claimed is:

1. A process for producing para-xylene and ethylbenzene from $C_8$ aromatics containing ethylbenzene, comprising the following steps:
    (1) sending a $C_8$ aromatics feed stream containing ethylbenzene to an ethylbenzene liquid-phase adsorption separation device, so that the ethylbenzene therein is adsorbed by a first adsorbent in an ethylbenzene adsorbent bed, and components not adsorbed by the first adsorbent are discharged from the ethylbenzene adsorbent bed as an adsorption residual liquid; rinsing the ethylbenzene adsorbent bed with a first desorbent to desorb the ethylbenzene therein and obtain an effluent, removing the first desorbent in the effluent to obtain ethylbenzene, and removing the first desorbent in the adsorption residual liquid to obtain an adsorption residual oil;
    (2) feeding the adsorption residual oil obtained in step (1) to a para-xylene adsorption separation device, wherein the para-xylene is adsorbed by a second adsorbent in a para-xylene adsorbent bed, and components not adsorbed are discharged from the adsorbent bed as a raffinate; rinsing the para-xylene adsorbent bed with a second desorbent to desorb the para-xylene therein and obtain an extract, and removing the second desorbent in the extract to obtain a para-xylene product stream, and removing the second desorbent from the raffinate oil; and
    (3) feeding the raffinate oil obtained in step (2) to a xylene isomerization device to carry out xylene isomerization in presence of a xylene isomerization catalyst, fractionating the isomerization product to obtain a $C_7$– aromatics fraction, a $C_8$ aromatics-containing fraction, discharging the $C_7$– aromatics fraction, and feeding the $C_8$ aromatics-containing fraction to the para-xylene adsorption separation device.

2. The process according to claim 1, wherein, in step (1), the ethylbenzene liquid-phase adsorption separation device is a first liquid-phase simulated moving bed operating at a temperature of 70 to 180° C. and a pressure of 0.2 to 2.0 MPa.

3. The process according to claim 2, wherein number of adsorbent beds of the first liquid-phase simulated moving bed is 8 to 24.

4. The process according to claim 1, wherein the ethylbenzene adsorbent comprises 95-99.5 mass % of CsNaX zeolite and 0.5-5 mass % of binder, wherein a molar ratio of Cs/Na is 1.5-10.0, and the first desorbent is toluene.

5. The process according to claim 1, wherein the ethylbenzene adsorbent comprises 95-99.5 mass % of X zeolite and 0.5-5 mass % of binder, wherein a cation site of the X zeolite is occupied by Ba or Ba and K, and the first desorbent is benzene.

6. The process according to claim 5, wherein a Na$_2$O content in the ethylbenzene adsorbent is less than 0.6 mass %; when the cation site of the X zeolite is occupied by Ba, the content of BaO in the adsorbent is 35-45 mass %; and when the cation site of the X zeolite is occupied by Ba and K, the content of BaO in the adsorbent is 25-35 mass % and the K$_2$O content is 7-10 mass %.

7. The process according to claim 4, wherein the first desorbent has a water content of 1 to 15 ppm.

8. The process according to claim 5, wherein the desorbent has a water content of 50 to 100 ppm.

9. The process according to claim 4, wherein a ratio of a volumetric flow of the first desorbent to a volumetric flow of the C$_8$ aromatics feed stream is 0.6 to 5.0 or 0.6 to 3.0.

10. The process according to claim 1, wherein, in step (2), the para-xylene liquid-phase adsorption separation device is a second liquid-phase simulated moving bed operating at a temperature of 110 to 200° C. and a pressure of 0.4 to 2.0 MPa.

11. The process according to claim 10, wherein a number of adsorbent beds of the second liquid-phase simulated moving bed is 8 to 24.

12. The process according to claim 1, wherein the para-xylene adsorbent comprises 95-99.5 mass % of X zeolite and 0.5-5 mass % of binder, wherein a cation site of the X zeolite is occupied by Ba or Ba and K.

13. The process according to claim 1, wherein the second desorbent is toluene or para-diethylbenzene.

14. The process according to claim 1, wherein xylene isomerization is carried out at a temperature of 210-360° C. and a pressure of 0.1-4.0 MPa, a weight hourly space velocity of the raffinate oil passing through the catalyst of 11-20 h$^{-1}$, and a hydrogen/hydrocarbon molar ratio of 0-0.9.

15. The process according to claim 1, wherein the isomerization product is fractionated to obtain the C$_7$– aromatics fraction, a C$_8$ aromatics fraction, and a C$_{9+}$ aromatics fraction, and the C$_7$– aromatics fraction and the C$_9$+ aromatics fraction are discharged, and the C$_8$ aromatics fraction is fed to the para-xylene adsorption separation device.

16. The process according to claim 1, further comprising feeding an external stream containing C$_8$ aromatics to the para-xylene adsorption separation device.

17. The process according to claim 16, wherein a mass ratio of the external stream containing C$_8$ aromatics component to the adsorption residual oil obtained in step (1) is 0.1 to 0.8.

18. The process according to claim 1, wherein the C$_8$ aromatics feed stream contains 10 to 25 mass % of C$_8$ aromatics.

19. The process according to claim 1, wherein the adsorption residual oil obtained in step (1) or the external stream containing C$_8$ aromatics contains not more than 3 mass % of C$_8$ aromatics.

20. The process according to claim 1, wherein the xylene isomerization catalyst in step (3) comprises 15-90 mass % of a zeolite and 10-85 mass % of alumina, wherein the zeolite is ZSM-5, ZSM-11, or a mixture thereof.

21. The process according to claim 1, wherein the xylene isomerization catalyst comprises 15-90 mass % of a zeolite, 1-5 mass % of mordenite, and 5-84 mass % of alumina, wherein the zeolite is ZSM-5, ZSM-11, or a mixture thereof.

* * * * *